US012734080B2

(12) United States Patent
Chen et al.

(10) Patent No.: US 12,734,080 B2
(45) Date of Patent: Sep. 15, 2026

(54) TWO PHASE ABSORBENT COMPOSITES

(71) Applicant: Kimberly-Clark Worldwide, Inc., Neenah, WI (US)

(72) Inventors: Feng Chen, Roswell, GA (US); Jian Qin, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 92 days.

(21) Appl. No.: 17/911,848

(22) PCT Filed: Apr. 30, 2020

(86) PCT No.: PCT/US2020/030601
§ 371 (c)(1),
(2) Date: Sep. 15, 2022

(87) PCT Pub. No.: WO2021/221639
PCT Pub. Date: Nov. 4, 2021

(65) Prior Publication Data

US 2023/0015099 A1 Jan. 19, 2023

(51) Int. Cl.
*A61F 13/53* (2006.01)

(52) U.S. Cl.
CPC .. *A61F 13/53* (2013.01); *A61F 2013/530489* (2013.01); *A61F 2013/530693* (2013.01); *A61F 2013/530744* (2013.01)

(58) Field of Classification Search
CPC .......... A61F 13/53; A61F 2013/530481; A61F 2013/530744; A61L 15/60
See application file for complete search history.

(56) References Cited

U.S. PATENT DOCUMENTS

| | | | |
|---|---|---|---|
| 6,124,391 | A | 9/2000 | Sun et al. |
| 7,205,259 | B2 | 4/2007 | Soerens |
| 7,329,701 | B2 | 2/2008 | Herfert et al. |
| 8,273,817 | B2 | 9/2012 | Gustafson et al. |
| 8,466,228 | B2 | 6/2013 | Smith et al. |

(Continued)

FOREIGN PATENT DOCUMENTS

| | | | |
|---|---|---|---|
| CN | 102245218 A | | 11/2011 |
| CN | 110776678 | * | 2/2020 |

(Continued)

OTHER PUBLICATIONS

Cheng et al., Effects of process and source on elastic modulus of single cellulose fibrils evaluated by atomic force microscopy, Composites Part A; Applied science and Manufacturing, vol. 40, Issue 5, May 2009, pp. 583-588 (Year: 2009).*

(Continued)

*Primary Examiner* — Camie S Thompson

(57) ABSTRACT

Described herein are absorbent composites containing a superabsorbent material and a fibril filler substantially distributed throughout the superabsorbent material. Also described herein are methods of producing absorbent composites containing a superabsorbent material and a fibril filler substantially distributed throughout the superabsorbent material. Compositions and methods described herein are useful in a variety of absorbent products.

15 Claims, 1 Drawing Sheet

(56) References Cited

U.S. PATENT DOCUMENTS

| | | | | |
|---|---|---|---|---|
| 8,486,854 | B2 | 7/2013 | Berrada et al. | |
| 8,962,910 | B2 | 2/2015 | Azad et al. | |
| 9,555,148 | B2 | 1/2017 | Wattebled et al. | |
| 9,687,579 | B2 | 6/2017 | Lindner et al. | |
| 9,688,781 | B2 | 6/2017 | Meyer et al. | |
| 9,861,071 | B2 | 1/2018 | Fritter et al. | |
| 9,919,274 | B2 * | 3/2018 | Mitra | B01D 67/0095 |
| 9,963,835 | B2 | 5/2018 | Tetrault et al. | |
| 10,178,834 | B2 | 1/2019 | Zhang et al. | |
| 10,258,962 | B2 | 4/2019 | Kim et al. | |
| 2005/0245393 | A1 | 11/2005 | Herfert et al. | |
| 2008/0249221 | A1 * | 10/2008 | Corkery | C09J 11/04 524/404 |
| 2010/0301027 | A1 * | 12/2010 | Sercel | B23K 26/0613 219/121.72 |
| 2012/0289607 | A1 | 11/2012 | Xiong et al. | |
| 2017/0361305 | A1 | 12/2017 | Kim et al. | |
| 2018/0305517 | A1 | 10/2018 | Kamphus et al. | |
| 2019/0309135 | A1 * | 10/2019 | Aronoff | B29C 48/022 |

FOREIGN PATENT DOCUMENTS

| | | | |
|---|---|---|---|
| CN | 116813947 | * | 9/2023 |
| KR | 101584719 | B1 | 1/2016 |
| KR | 101911936 | B1 | 10/2018 |
| WO | 2006118807 | A1 | 11/2006 |
| WO | 2009041870 | A1 | 4/2009 |
| WO | 2014094892 | A1 | 6/2014 |

OTHER PUBLICATIONS

El Miri et al., Bio-nanocomposite films reinforced with cellulose nanocrystals: Rheology of film Forming Solutions, Transparency, Water Vapor Barrier and Tensile Properties of Films, Carbohydrate Polymers, 129:156-167, Sep. 2015. (Year: 2015).*

Dmitriev et al., Hybrid hydrogels based on cross-linked polyacrylic acid and polyvinyl alcohol as electrically controlled artificial muscles, November 2016Russian Journal of Applied Chemistry 89(11):1838-1845.*

Wikipedia, Nanotube, accessed online Aug. 1, 2026.*

Hybrid hydrogels based on cross-linked polyacrylic acid and polyvinyl alcohol as electrically controlled artificial muscles, Nov. 2016, Russian Journal of Applied Chemistry,89(11), 1838-1845 (Year: 2016).*

Elastic modulus of halloysite nanotubes, Nanotechnology, Mar. 15, 2013, 24(10). (Year: 2013).*

Wang, Yanfei et al., "Synthesis of poly(AA-co-AM) superabsorbent composites by reinforcement of halloysite nanotubes"; DOI 10.1002/pc.22934; Polymer Composites; vol. 36, Issue 2, Feb. 18, 2014; pp. 229-236.

Irani, Maryam et al., "Hydrogel composites based on linear low-density polyethylene-g-poly (acrylic acid)/Kaolin or halloysite nanotubes"; DOI 10.1002/app.40101; Journal of Applied Polymer Science; vol. 131, Issue 8; 12 pp.

Pandey, Priyal et al., "Halloysite Nanoclay Polymer Composite: Synthesis, Characterization and Effect on Water Retention Behaviour of Soil"; DOI 10.9734/CSJI/2018/42613; Chemical Science International Journal; vol. 23, Issue 3, Jul. 5, 2018; 11 pp.

PCT International Preliminary Report on Patentability for International Application PCT/US2020/030601 mailed Jun. 30, 2021; 7 pp.

PCT International Search Report and Written Opinion for Patent Application PCT/US2020/030601 mailed Apr. 30, 2020; 12 pp.

Liu, Chuochuo et al., "Preparation of poly(sodium acrylate-acrylamide) superabsorbent nanocomposites incorporating graphene oxide and halloysite nanotubes"; DOI 10.1039/C3RA23094E; Royal Science of Chemistry, Issue 33, vol. 3, 2013; pp. 13756-13763.

* cited by examiner

TWO PHASE ABSORBENT COMPOSITES

FIELD OF DISCLOSURE

The present disclosure is directed to absorbent composites including a superabsorbent material and a fibril filler substantially distributed throughout the superabsorbent material. The absorbent composites have improved absorption under load as compared to conventional absorbent composites. This disclosure is also directed to methods of producing absorbent composites containing a superabsorbent material and a fibril filler substantially distributed throughout the superabsorbent material. Compositions and methods in accordance with the present disclosure are useful in a variety of absorbent products.

BACKGROUND

Super absorbent materials (SAMs) are three-dimensional networks that can absorb and retain water (or other aqueous media) and physiological fluids such as urine and blood more than hundreds times of their own dry weight, typically depending on the ionic concentration of the aqueous solution. SAMs have applications in a variety of fields, including medicine, construction, personal care products, biomaterials, biosorbents, and agriculture. SAMs were industrially developed in Japan and USA in the early 1980s for hygienic applications. It was found that SAMs had the potential to replace fluff, making their use in hygienic products such as baby diapers and feminine napkins cost effective.

For products containing SAMs, and especially those products in personal hygiene product applications, it is important to improve the performance of SAMs in terms of absorbency under load (AUL) and centrifuge retention capacity (CRC). AUL represents the capability of SAMs to absorb liquid and retain the absorbed liquid even under stress. Retention of absorbed liquid under stress generally occurs in hygienic products when the hygiene product is worn duo to the movements of the wearer.

SAMs in a solid state should have a high strength (i.e. high elastic modulus), so that the particles of the SAMs do not crush and convert into a fine powder when processed, worn, and/or stored. Similarly. SAMs in a swollen state (i.e. hydrogel) should also have a high elastic modulus, so that the swollen gel does not become crushed and release the absorbed liquid after absorption. There is a significant need to reinforce SAMs in both the gel state and the original solid state to improve the AUL and other properties.

Attempted improvements to reinforce SAMs are known in the art. As one representative example, U.S. Pat. No. 8,962,910 discloses superabsorbent polymers containing clay particulates and methods of making the same. The clay particulates are made of kaolin, which has a relatively low degree of layered structure of bentonite. The clay was added to the gel after gel formation instead of before polymerization. However, when the clay was added after the gel was formed, the clay could only be added onto the gel particles, and therefore the gels do not exhibit the reinforced results obtained by uniformly dispersing the clay throughout the matrix of the gel bulk phase. Rather, such processing methods are typically for increasing surface friction between SAM particles and therefore increase gel bed permeability (GBP).

As another representative example, Wang et al. reported the synthesis of poly(AA-co-AM) superabsorbent composites by reinforcement of halloysite nanotubes (Wang et al., *Polym. Compos.,* 2014; 36: 229-236). However, the optimum properties of such superabsorbents require a molar ratio of acrylamide (AM) over acrylic acid (AA) of 0.6:1, which indicates the necessity of AM composition in the co-polymer. Further, no data were provided for the composite with 0% halloysite nanotubes, and there is no suggestion that the absorbency properties increased due to the addition of halloysite nanotubes. In addition, the copolymer and halloysite clay formed a porous structure with 10 μm pore sizes, which also contributes significantly to absorption. Finally, the mechanism of forming porous structures is not provided.

Utilizing rigid fillers to reinforce polymer matrices is known in the polymer industry to increase the strength and modulus of final products. Common reinforcing fillers include glass fiber and silica powder, which can increase the strength of polymer composites used for aircraft, trains and cars, and can also provide lighter weights compared with traditional metallic parts.

Fibril fillers are known to provide a reinforcing effect with less filler amounts compared to spherical fillers. For example, Chen et al. (Chen et al., *Polymer,* 2010, 51: 1812-1819) added soy protein to reinforce a polybutylene adipate-co-terephthalate (PBAT) matrix because soy protein has higher elastic modulus compared to polymer matrix PBAT and can be modified to an elongated shape during blending and extrusion.

Described herein is a novel solution to the problem of unreinforced SAMs with low elastic modulus. A fibril filler is incorporated into a SAM during the synthesis process. The morphology of the fibril filler should be tube-like to impart the maximum reinforcement. Because the elastic modulus of the fibril filler is higher than that of the SAM material, the incorporation of fibril filler reinforces the SAM structure in both solid and gel states. Increased gel strength can further increase AUL.

Compositions and methods in accordance with the present disclosure are useful in a variety of absorbent products. Any conventional product containing a superabsorbent ingredient could benefit from the compositions and methods in accordance with the present disclosure. Such products include, but are not limited to, personal hygiene products, baby and adult diaper products, feminine pads, arm bands, products for agricultural usage, and cat litter products.

BRIEF DESCRIPTION OF THE DISCLOSURE

In one embodiment of the present disclosure, provided herein is an absorbent composite. The absorbent composite includes a superabsorbent material and a fibril filler substantially distributed throughout the superabsorbent material.

In another embodiment of the present disclosure, provided herein is a method of producing an absorbent composite. The method includes: (i) forming a mixture including a polymerizable monomer of a superabsorbent material, a fibril filler, water, optionally a neutralization agent, optionally an initiator, and optionally a crosslinker, and (ii) polymerizing the polymerizable monomer of a superabsorbent material in the mixture to produce an absorbent composite comprising a superabsorbent material and the fibril filler; wherein the fibril filler is substantially distributed throughout the superabsorbent material in the absorbent composite.

In yet another embodiment of the present disclosure, provided herein is a use of an absorbent composite in a consumer product. The used absorbent composite includes a superabsorbent material and a fibril filler substantially distributed throughout the superabsorbent material.

DETAILED DESCRIPTION OF THE DISCLOSURE

Figure 1A:
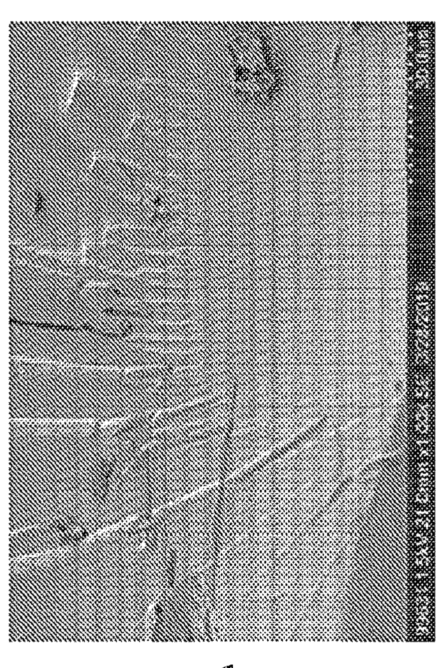
FIG. 1A is an exemplary embodiment of an SEM image of the morphology of a SAM control sample not in accordance with the present disclosure.

Generally speaking, the present disclosure relates to multiple embodiments of novel two phase absorbent composites that include a superabsorbent material and a fibril filler substantially distributed throughout the superabsorbent material. In many embodiments, the fibril filler substantially distributed throughout the superabsorbent material increases the overall performance of the superabsorbent particles in a product, such as an absorbent product for example. The superabsorbent particles present in the absorbent composites may be in one or more various forms in accordance with the present disclosure.

As used herein, a fibril filler is a filler material with a tube-like structure. Fibril fillers include any tube-like structure having fibrillar morphology. Such tube-like structures of sufficient morphology include, but are not limited to, nanotubes, natural hollow fibers, synthetic hollow fibers, and combinations thereof. The morphology of the fibril filler can be any elongated shape with an aspect ratio larger than 1.

One advantage of fibril filler over other fillers is its large aspect ratio; the probability of such fillers forming a percolated and/or network structure is much higher than for fillers with other shapes, such as particulates. It is well recognized that the properties of polymer composites show a significant increase when the filler phase forms a percolated/network structure in the matrix phase. Further, the percentage of filler amount is a very important factor to form such a percolated structure. With fibril filler, the required amount of filler is greatly reduced compared to other shapes, such as particulates.

In some embodiments, the fibril filler is in a form selected from the group consisting of tube-like structures with an aspect ratio larger than 1, nanotubes, natural hollow fibers, synthetic hollow fibers, and combinations thereof. In some embodiments, the fibril filler is in a form consisting essentially of nanotubes. In some embodiments, the fibril filler is in a form consisting of nanotubes. In some embodiments, the fibril filler is in a form that is substantially one-dimensional.

The fibril filler is not in a form selected from the group consisting of nanoplates, spherical particles, substantially spherical particles, and combinations thereof. Non-fibrillar morphologies do not provide desirable properties in absorbent composites. For example, based on the study from Chen et al. (Chen et al., *ACS Appl. Mater. Interfaces,* 2010, 2, 3324-3332), polybutylene adipate-co-terephthalate (PBAT) blends containing soy protein filler phase with different aspect ratios showed totally different reinforcing effects for strengthening the PBAT matrix. The reinforcing effect is much higher for the blend with high aspect ratio fillers compared to those with low aspect ratios, which leads to higher mechanical properties of the final polymer composite.

In some embodiments, the fibril filler has a diameter in the range of from about 1 nm to about 100 nm. In some embodiments, the fibril filler has a diameter in the range of from about 10 nm to about 100 nm. In some embodiments, the fibril filler has a diameter in the range of from about 25 nm to about 75 nm.

In some embodiments, the fibril filler has a length in the range of from about 0.01 μm to about 10 μm. In some embodiments, the fibril filler has a length in the range of from about 0.1 μm to about 10 μm. In some embodiments, the fibril filler has a length in the range of from about 0.5 μm to about 5 μm. In some embodiments, the fibril filler has a length in the range of from about 1 μm to about 3 μm.

In some embodiments, the fibril filler has an aspect ratio in the range of from about 1:1 to about 100:1. In some embodiments, the fibril filler has an aspect ratio in the range of from about 1:1 to about 30:1. In some embodiments, the fibril filler has an aspect ratio in the range of from about 5:1 to about 20:1.

The fibril filler may comprise conventional filler materials known to impart desirable properties, such as improved elastic modulus, to absorbent composites. In some embodiments, the fibril filler comprises a material selected from the group consisting of inorganic materials, clays, aluminosilicates, halloysite, glass fibers, carbon nanotubes, plant fibers, elongated second phases, and combinations thereof. In some embodiments, the fibril filler comprises halloysite.

Elastic modulus measures a material's resistance to being deformed elastically when a stress is applied to it. The fibril filler typically has a higher elastic modulus than the superabsorbent material. In many embodiments, the fibril filler has an elastic modulus that is greater than the elastic modulus of the superabsorbent material. Distributing the fibril filler throughout the superabsorbent material increases the elastic modulus and produces a composite material of higher elastic modulus than the superabsorbent material.

In some embodiments, the fibril filler is present in an amount of less than about 15 wt %. In some embodiments, the fibril filler is present in an amount of less than about 14 wt %. In some embodiments, the fibril filler is present in an amount of less than about 13 wt %. In some embodiments, the fibril filler is present in an amount of less than about 12 wt %. In some embodiments, the fibril filler is present in an amount of loss than about 11 wt %. In some embodiments, the fibril filler is present in an amount of less than about 10 wt %. In some embodiments, the fibril filler is present in an amount of less than about 9 wt %. In some embodiments, the fibril filler is present in an amount of loss than about 8 wt %. In some embodiments, the fibril filler is present in an amount of less than about 7 wt %. In some embodiments, the fibril filler is present in an amount of less than about 6 wt %. In some embodiments, the fibril filler is present in an amount of less than about 5 wt %. In some embodiments, the fibril filler is present in an amount of less than about 4 wt %. In some embodiments, the fibril filler is present in an amount of less than about 3 wt %. In some embodiments, the fibril filler is present in an amount of less than about 2 wt %. In some embodiments, the fibril filler is present in an amount of less than about 1 wt %.

In some embodiments, the fibril filler is present in an amount of greater than about 0 wt %. In some embodiments, the fibril filler is present in an amount of greater than about 1 wt %. In some embodiments, the fibril filler is present in an amount of greater than about 2 wt %. In some embodiments, the fibril filler is present in an amount of greater than about 3 wt %. In some embodiments, the fibril filler is present in an amount of greater than about 4 wt %. In some embodiments, the fibril filler is present in an amount of greater than about 5 wt %. In some embodiments, the fibril filler is present in an amount of greater than about 6 wt %. In some embodiments, the fibril filler is present in an amount of greater than about 7 wt %. In some embodiments, the fibril filler is present in an amount of greater than about 8 wt %. In some embodiments, the fibril filler is present in an amount of greater than about 9 wt %. In some embodiments, the fibril filler is present in an amount of greater than about 10 wt %. In some embodiments, the fibril filler is present in an amount of greater than about 11 wt %. In some embodiments, the fibril filler is present in an amount of greater than about 12 wt %. In some embodiments, the fibril filler is present in an amount of greater than about 13 wt %. In some embodiments, the fibril filler is present in an amount of greater than about 14 wt %.

In some embodiments, the fibril filler is present in an amount in the range between 0% and 15%. In some embodiments, the fibril filler is present in an amount in the range between 0% and 10%. In some embodiments, the fibril filler is present in an amount in the range between 5% and 15%. In some embodiments, the fibril filler is present in an amount in the range between 5% and 10%.

The fibril filler is substantially distributed throughout the superabsorbent material to provide the required support and absorbency properties. Absorbent composites not including fibril fillers, and absorbent composites including fibril fillers but not including said fibril fillers substantially distributed throughout the superabsorbent material, do not provide the required support and absorbency properties.

In many embodiments, the fibril filler is substantially distributed throughout the superabsorbent material. In many embodiments, the superabsorbent material comprises a polymer matrix. In some embodiments, the fibril filler is substantially distributed throughout the superabsorbent material matrix. In some embodiments, the fibril filler is substantially distributed on a surface layer of the superabsorbent material. The fibril filler being substantially distributed on a surface layer of superabsorbent material differs from the fibril filler being coated on the surface of the superabsorbent material.

In some embodiments, substantially distributed means that the fibril filler is distributed in an amount greater than about 70% uniformity. In some embodiments, substantially distributed means that the fibril filler is distributed in an amount greater than about 80% uniformity. In some embodiments, substantially distributed means that the fibril filler is distributed in an amount greater than about 90% uniformity. In some embodiments, substantially distributed means that the fibril filler is distributed in an amount greater than about 95% uniformity. In some embodiments, substantially distributed means that the fibril filler is distributed in an amount greater than about 99% uniformity. In some embodiments, the fibril filler is uniformly distributed throughout the superabsorbent material.

The superabsorbent material may comprise conventional superabsorbent materials known to impart desirable properties to absorbent composites. In some embodiments, the superabsorbent material comprises a polymer comprising a polymerizable monomer selected from the group consisting of 2-acrylamido-2-methylpropane sulfonic acid, methacrylate monomers with tethered sulfate groups, salts of vinyl-linker-acid units, vinylic sulfate monomers, acrylic acids, vinyl sulfonic acids, vinyl phosphoric acids, and combinations thereof. In some embodiments, the superabsorbent material comprises a polymer selected from the group consisting of polyacrylic acid (PAA), poly(2-acrylamido-2-methyl-1-propanesulfonic acid) (polyAMPS), partially hydrolyzed maleic anhydrides, sodium alginate, chitosan salt, modified starches, modified natural polymers, modified cellulose, pre-polymers, and combinations thereof.

The degree of neutralization is about 70% in conventional commercial superabsorbent materials. In general, the higher the degree of neutralization a superabsorbent material has, the higher the absorbency the superabsorbent material exhibits. This indicates that it is preferred to have a degree of neutralization as high as possible for achieving the highest absorbent efficiency. On the other hand, fully neutralized superabsorbent materials, having 100% degree of neutralization, result in a basic pH when saturated by urine, which would cause skin irritation for a wearer in skin contact with the fully neutralized superabsorbent materials. Human skin prefers a slightly acidic to near neutral pH value. Therefore, a degree of neutralization around 70% can achieve a safe and skin friendly pH value.

The superabsorbent material has a substantial degree of neutralization. In some embodiments, the superabsorbent material has a degree of neutralization greater than about 50%. In some embodiments, the superabsorbent material has a degree of neutralization greater than about 60%. In some embodiments, the superabsorbent material has a degree of neutralization greater than about 70%. In some embodiments, the superabsorbent material has a degree of neutralization greater than about 80%. In some embodiments, the superabsorbent material has a degree of neutralization greater than about 90%. In some embodiments, the superabsorbent material has a degree of neutralization greater than about 95%. In some embodiments, the superabsorbent material has a degree of neutralization greater than about 99%.

The superabsorbent material has a substantially high modulus. If the modulus is too low, then the fibril filler does not impart the desired properties.

The absorbent composite may further comprise a crosslinker. Suitable crosslinkers include conventional crosslinkers. In some embodiments, the crosslinker comprises at least two double bonds.

In some embodiments, the crosslinker is selected from the group consisting of tetraallyloxyethane, N, N'-methylene bisacryl amide, N, N'-methylene bismethacrylamide, triallylamine, trimethylol propane triacrylate, glycerol propoxy triacrylate, divinylbenzene, N-methylol acrylamide, N-methylol methacrylamide, glycidyl methacrylate, polyethylene, polyamines, ethyl diamine, ethyl glycol, glycerin, tetraallyloxyethane and triallyl ethers of pentaerythritol, aluminates, silica, alumosilicates, and combinations thereof.

In many embodiments, the modulus of the superabsorbent material can be defined according to the crosslinking density because the modulus of the superabsorbent material is directly proportional to the crosslinking density. In some embodiments, the crosslinking density of the absorbent composite is in the range of from about 1 mol % to about 8 mol %. In some embodiments, the crosslinking density of the absorbent composite is in the range of from about 2 mol % to about 6 mol %. In some embodiments, the crosslinking density of the absorbent composite is in the range of from about 3 mol % to about 5 mol %.

In many embodiments, the absorbent composite has an elastic modulus that is greater than the elastic modulus of the superabsorbent material. In many embodiments, the absorbent composite has an elastic modulus that is less than the elastic modulus of the fibril filler. In some embodiments, the absorbent composite has an elastic modulus that is greater than the elastic modulus of the superabsorbent material and less than the elastic modulus of the fibril filler.

Absorbent composites according to the present disclosure may be produced according to any suitable methods. In one specific embodiment, a method may comprise forming a mixture comprising a polymerizable monomer of a superabsorbent material, a fibril filler, water, optionally a neutralization agent, optionally an initiator, and optionally a crosslinker; and polymerizing the polymerizable monomer of a superabsorbent material in the mixture to produce an absorbent composite comprising a superabsorbent material and the fibril filler. In this method, the fibril filler is substantially distributed throughout the superabsorbent material in the absorbent composite.

In some embodiments, the formed mixture is substantially homogenous. In some embodiments, the formed mixture is homogenous.

In some embodiments, the method step of forming a mixture comprises a method selected from the group consisting of stirring the mixture, cooling the mixture, heating the mixture, degassing the mixture, degassing the mixture with $N_2$, and combinations thereof. In some embodiments, the mixture is cooled to a temperature in the range of from about −20° C. to about 20° C. In some embodiments, the mixture is cooled to about 0° C.

In some embodiments, the mixture may further comprise a neutralization agent. In some embodiments, the neutralization agent is a strong base selected from the group consisting of sodium hydroxide, potassium hydroxide, ammonium hydroxide, sodium bicarbonate, sodium carbonate, potassium carbonate, and combinations thereof.

In some embodiments, the method step of polymerizing the polymerizable monomer of a superabsorbent material in the mixture is according to a method selected from free radical polymerization, anionic polymerization, cationic polymerization, controlled radical polymerization methods, atom-transfer radical-polymerization (ATRP), nitroxide mediated radical polymerization (NMP), reversible addition-fragmentation chain-transfer polymerization (RAFT), and combinations thereof. In some embodiments, the polymerizable monomer is polymerized according to free radical polymerization.

In some embodiments, the method step of polymerizing the polymerizable monomer of a superabsorbent material in the mixture comprises adding an initiator to the mixture. In some embodiments, the initiator is a free radical initiator.

In some embodiments, the initiator is an azo compound (R—N═N—R'); such an azo compound is the precursor of two carbon-centered radicals (R· and R'·) and nitrogen gas upon heating and/or by irradiation. For example, azobisisobutyronitrile (AIBN) and 1,1'-azobis(cyclohexanecarbonitrile) (ABCN) yield isobutyronitrile and cyclohexanecarbonitrile radicals, respectively.

In some embodiments, the initiator is an organic peroxide. Organic peroxides each have a peroxide bond (—O—O—), which is readily cleaved to yield two oxygen-centered radicals. The oxyl radicals are unstable and believed to be transformed into relatively stable carbon-centered radicals. For example, di-tert-butyl peroxide (tBuOOtBu) yields two t-butoxy radicals (tBuO·) and the radicals become methyl radicals ($CH_3$·) with the loss of acetone. Benzoyl peroxide ($(PhCOO)_2$) generates benzoyloxyl radicals (PhCOO·), each of which loses carbon dioxide to be converted into a phenyl radical (Ph·). Methyl ethyl ketone peroxide is also common, and acetone peroxide may be used as a radical initiator, too.

In some embodiments, the initiator is an oxidizing agent. In some embodiments, the initiator is an inorganic peroxide or persulfate. Examples include potassium persulfate, ammonium persulfate, peroxydisulfate, and hydrogen peroxide.

In some embodiments, the initiator is selected from the group consisting of azo compounds, organic peroxides, inorganic peroxides, inorganic persulfates, and combinations thereof. In some embodiments, the initiator is selected from the group consisting of AIBN, ABCN, di-tert-butyl peroxide, benzoyl peroxide, methyl ethyl ketone peroxide, acetone peroxide, potassium persulfate, ammonium persulfate, peroxydisulfate, hydrogen peroxide, and combinations thereof.

In some embodiments, the method further comprises adding an initiator to the mixture during polymerization.

In some embodiments, the method step of polymerizing the polymerizable monomer of a superabsorbent material in the mixture comprises polymerizing the polymerizable monomer of a superabsorbent material in the mixture in an inert atmosphere. In some embodiments, the method step of polymerizing the polymerizable monomer of a superabsorbent material in the mixture comprises polymerizing the polymerizable monomer of a superabsorbent material in the mixture in a static inert atmosphere. In some embodiments, the method step of polymerizing the polymerizable monomer of a superabsorbent material in the mixture comprises polymerizing the polymerizable monomer of a superabsorbent material in the mixture in a dynamic inert atmosphere. In some embodiments, the method step of polymerizing the polymerizable monomer of a superabsorbent material in the mixture comprises polymerizing the polymerizable monomer of a superabsorbent material it the mixture under a flow of an inert gas.

In some embodiments, the method step of polymerizing the polymerizable monomer of a superabsorbent material in the mixture comprises polymerizing the polymerizable monomer of a superabsorbent material in the mixture in an inert atmosphere selected from $N_2$, $CO_2$, noble gases, helium, neon, argon, krypton, xenon, and a combination thereof. In some embodiments, the method step of polymerizing the polymerizable monomer of a superabsorbent material in the mixture comprises polymerizing the polymerizable monomer of a superabsorbent material in the mixture in an inert atmosphere of $N_2$.

In some embodiments, the method step of polymerizing the polymerizable monomer of a superabsorbent material in the mixture comprises heating the mixture. In some embodiments, the method step of polymerizing the polymerizable monomer of a superabsorbent material in the mixture comprises heating the mixture to a temperature in the range of from about 30° C. to about 100° C. In some embodiments, the method step of polymerizing the polymerizable monomer of a superabsorbent material in the mixture comprises heating the mixture to a temperature in the range of from about 40° C. to about 90° C. In some embodiments, the method step of polymerizing the polymerizable monomer of a superabsorbent material in the mixture comprises heating the mixture to a temperature in the range of from about 50° C. to about 80° C. In some embodiments, the method step of polymerizing the polymerizable monomer of a superabsorbent material in the mixture comprises heating the mixture to a temperature in the range of from about 60° C. to about 70° C.

In some embodiments, the method step of polymerizing the polymerizable monomer of a superabsorbent material in the mixture comprises heating the mixture to a temperature in the range of from about 30° C. to about 90° C. In some embodiments, the method step of polymerizing the polymerizable monomer of a superabsorbent material in the mixture comprises heating the mixture to a temperature in the range of from about 30° C. to about 80° C. In some embodiments, the method step of polymerizing the polymerizable monomer of a superabsorbent material in the mixture comprises heating the mixture to a temperature in the range of from about 40° C. to about 70° C. In some embodiments, the method step of polymerizing the polymerizable monomer of a superabsorbent material in the mixture comprises heating the mixture to a temperature in the range of from about 50° C. to about 70° C.

In some embodiments, the method step of polymerizing the polymerizable monomer of a superabsorbent material in the mixture comprises heating the mixture to a temperature in the range of from about 50° C. to about 70° C. In some embodiments, the method step of polymerizing the polymerizable monomer of a superabsorbent material in the mixture comprises heating the mixture to about 60° C. In some embodiments, the method step of polymerizing the polymerizable monomer of a superabsorbent material in the mixture comprises heating the mixture to about 70° C.

In some embodiments, the method further comprises drying the absorbent composite. In some embodiments, the method further comprises drying the absorbent composite in an oven. In some embodiments, the method further comprises drying the absorbent composite at a temperature in the range of from about 50° C. to about 100° C. In some embodiments, the method further comprises drying the absorbent composite at a temperature in the range of from about 60° C. to about 100° C. In some embodiments, the method further comprises drying the absorbent composite at a temperature in the range of from about 70° C. to about 100° C. In some embodiments, the method further comprises drying the absorbent composite at a temperature in the range of from about 80° C. to about 100° C. In some embodiments, the method further comprises drying the absorbent composite at a temperature in the range of from about 60° C. to about 90° C. In some embodiments, the method further comprises drying the absorbent composite at a temperature in the range of from about 70° C. to about 90° C.

In some embodiments, the method further comprises drying the absorbent composite at a temperature of about 85° C.

In some embodiments, the method further comprises grinding the dried absorbent composite. In some embodiments, the method further comprises grinding the dried reaction product with a grinding device selected from a mechanical blender, mechanical grinder, and combinations thereof.

In some embodiments, the polymerizable monomer of a superabsorbent material is partially polymerized before forming the mixture. In one specific embodiment, absorbent composites according to the present disclosure may be produced according to a method including: (i) forming a first mixture comprising a polymerizable monomer of a superabsorbent material, water, an initiator, optionally a neutralization agent, and optionally a crosslinker; (ii) partially polymerizing the polymerizable monomer of a superabsorbent material in the first mixture to form a second mixture; (iii) adding a fibril filler, additional initiator, and optionally a crosslinker to the second mixture to form a third mixture; (iv) mixing the third mixture; and (v) fully polymerizing the polymerizable monomer of a superabsorbent material to produce an absorbent composite comprising a superabsorbent material and the fibril filler. The fibril filler is substantially distributed throughout the superabsorbent material in the absorbent composite.

In some embodiments, the ability of a polymer to absorb fluid under a static load can be measured as absorbance under load (AUL). A typical AUL test format may be used.

In some embodiments, the capacity of a pre-swollen polymer to retain water under force can be measured as centrifuge retention capacity (CRC). A typical CRC test format may be used.

In some embodiments, the time between initial addition of dry SAM into a fixed volume of saline with a fixed speed of rotation and the time its rotational vortex completely disappears can be measured as vortex time. A typical vortex time test format may be used.

Absorbent composites according to the present disclosure may be used in a consumer product. In some embodiments, a consumer product comprises an absorbent composite according to the present disclosure.

In some embodiments, a method of using an absorbent composite according to the present disclosure comprises using the absorbent composite in a consumer product.

In some embodiments, the consumer product is selected from the group consisting of personal hygiene products, wipes, napkins, bibs, disposable bed liners, wound dressings, food packaging, baby and adult diaper products, child training pants, feminine pads, arm bands, agricultural and pet products that contain superabsorbent ingredients, disposable absorbent products, and combinations thereof.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever.

Materials.

Unless otherwise indicated, the following materials were used in the examples: Acrylic acid (AA), anhydrous, contains 200 ppm MEHQ as inhibitor, 99%; Potassium persulfate (KPS), 99.99%; N,N-Methylene(bis)acrylamide (MBAA), ≥99.5%; sodium hydroxide, anhydrous, free-flowing pellets, ≥97%; Halloysite nanoclay, a type of filler material with tube-like morphology; nanofibrillated cellulose EFTec Nanofibrillated Lyocell Fiber Type L-010-4, a nanofiber filler with fiber diameters in the range of between 50 to 500 nm; and Nanoclay 1.34 TCN, a surface modified nanoclay powder filler.

Mixture Formation.

The comparative examples and inventive examples were prepared according to the same general procedures. 10 g of acrylic acid monomer was added to a 120 mL wide mouth round jar with a magnetic stir bar. 40 mL of deionized water (DI $H_2O$) was added to the jar and then cooled down to about 0° C. with an ice water bath. 4 g of >97% NaOH pellets was added to the cold solution and then the mixture was stirred until NaOH pellets were fully dissolved by employing a magnetic stir bar.

For the comparative examples, 28 mg of 99.99% KPS and 28 mg >99% MBAA were added to the cold neutralized AA solution in DI-water.

For the inventive examples, halloysite clay powder was added to the mixture. Then 28 mg of 99.99% KPS and 28 mg >99% MBAA were added to the mixture, and another 130 mg of 99.99% KPS was added prior to the gelling process due to the consumption of radicals by clay. The synthesis was improved when the total amount of 130 mg was added by two additions of 65 mg to the solution.

Gel Polymerization.

Each respective mixture was rigorously degassed with high purity nitrogen for 5 minutes to remove trapped air in the reaction mixture and replace the air above the mixture in the glass container. After the degassing step, the glass reaction container was sealed and transferred to a pre-heated water bath equipped with a magnetic stirrer for the polymerization process. After 3 minutes, the desired amounts of filler were added into the solution, then the solution was degassed for 30 seconds and stirred well at the same time. The polymerization temperature was controlled at the ranges of from about 60-70° C. The gelling time was monitored (e.g. the time until the magnetic stir bar stops stirring) and after gelling, the gel stayed in the heating bath for an additional 4 hours to ensure the completion of the polymerization. After polymerization, the big gel block was removed from the glass reaction flask and cut into small chunks for easy drying using a knife or scissor.

Drying and Grinding.

All gels were dried in a convection oven at 85° C. for at least 48 hours. A 100 mg scaled mechanical blender was used to break up the big gel block into small pieces. A US Standard sieves set was used to collect particles with size range of 300-600 μm and 90-300 μm or particles with size range of 355-600 μm and 90-355 μm. Sieved particles were dried again overnight at 85° C. before testing.

Testing.

Absorbency under load (AUL), centrifuge retention capacity (CRC), and vortex time were tested according to previously reported standard procedures.

Absorbency Under Load (AUL) Test.

The AUL test is a measure of the ability of a superabsorbent material to absorb a liquid while the superabsorbent material is under a restraining load. This test was described in US 2003/0139715.

Briefly, a demand absorbency tester (DAT) 80 is used, which is similar to a GATS (gravimetric absorbency test system), available from M/K Systems, Danners, Mass., as well as a system described by Lichstein in pages 129-142 of the INDA Technological Symposium Proceedings, March 1974.

A porous plate is used having ports confined within the 2.5 centimeters diameter covered, in use, by the Absorbency Under Load apparatus. The porous plate has a diameter of 3.2 centimeters with 7 ports (holes) each with diameter of 0.30 centimeters. The porous plate has one hole in the center and the holes are spaced such that the distance from the center of one hole to another adjacent to it is 1.0 centimeter. An electrobalance is used to measure the flow of the test fluid (an aqueous solution containing 0.9% by weight sodium chloride) into the superabsorbent material.

The AUL apparatus used to contain the superabsorbent material may be made from 1 inch (2.54 centimeters), inside diameter, thermoplastic tubing machined-out slightly to be sure of concentricity. A #100 mesh stainless steel wire cloth is adhesively attached to the bottom of tubing. Alternatively, the steel wire cloth may be heated in a flame until red hot, after which the tubing is held onto the cloth until cooled. Care should be taken to maintain a flat, smooth bottom and not distort the inside of the tubing. A 4.4 gram piston may be made from 1 inch (2.54 centimeters) solid material (e.g., Plexiglas) and machined to closely fit, without binding, in the tubing. A 317 gram weight is used to provide 62,000 dynes per square centimeter (about 0.9 pounds per square inch (psi)) restraining load on the superabsorbent material. For the purpose of the present disclosure, the pressure applied during the AUL test is 0.9 psi.

Desirably, about 0.160 grams of superabsorbent is used. The sample is taken from superabsorbent material, which is pre-screened through U.S. standard #30 mesh screen and retained on U.S. standard #50 mesh screen. The superabsorbent material, therefore, has a particle size of about 300 to 600 microns. The particles may be pre-screened by hand or automatically pro-screened with, for example, a Ro-Tap Mechanical Sieve Shaker Model B available from W. S. Tyler, Inc., Mentor, Ohio.

The desired amount of superabsorbent material (0.160 grams) is weighed onto weigh paper and placed on the wire cloth at the bottom of the tubing. The tubing is shaken to level the superabsorbent material on the wire cloth. Care is taken to be sure no superabsorbent material is clinging to the wall of the tubing. The piston and weight are carefully placed on the superabsorbent material to be tested. The test is initiated by placing a 3 centimeter diameter glass filter paper (Whatman filter paper Grade GF/A, available from Whatman International Ltd., Maidstone, England) onto the plate (the paper is sized to be larger than the internal diameter and smaller than the outside diameter of the tubing) to ensure good contact, while eliminating evaporation over the ports of the demand absorbency tester and then allowing saturation to occur. The device is started by placing the apparatus on the glass filter paper and allowing saturation to occur. The amount of fluid picked up is monitored as a function of time either directly by hand, with a strip chart recorder, or directly into a data acquisition or personal computer system.

The amount of fluid pick-up measured after 60 minutes is the AUL value and is reported in grams of test liquid absorbed per gram of superabsorbent material as determined before starting the test procedure. A check can be made to ensure the accuracy of the test. The apparatus can be weighed before and after the test with a difference in weight equaling the fluid pick-up.

Centrifuge Retention Capacity Test

As used herein, the centrifugal retention capacity (CRC) is a measure of the absorbent capacity of the superabsorbent material or fiber after being subjected to centrifugation under controlled conditions. This test was described in US 2003/0139715.

Briefly, the superabsorbent sample to be tested is taken from superabsorbent material which is prescreened through U.S. standard #30 mesh and retained on U.S. standard #50 mesh to obtain a particle size of between 300 and 600 microns. Testing a fiber sample is performed “as-is” without fractionation. The CRC can be measured by placing 0.200 grams of the sample material to be tested (moisture content of less than 5 weight percent) into a water-permeable bag which will contain the sample while allowing the test solution (0.9 percent by weight sodium chloride solution) to be freely absorbed by the sample. A heat-sealable tea bag material (grade 542, commercially available from Kimberly-Clark Corporation, Neenah, Wis.) works well for most applications. The bag is formed by folding a 12.7 centimeter by 7.62 centimeter sample of the bag material in half and heat sealing two of the open edges to form a 6.35 by 7.62 centimeter rectangular pouch. The heat seals should be about 0.635 centimeters inside the edge of the material. After the sample is placed in the pouch, the remaining open edge of the pouch is also heat-sealed. Empty bags are also made to be tested with the sample bags as controls. Three sample bags are tested for each superabsorbent material. The sealed bags are placed between two Teflon coated fiberglass screens having 0.635 centimeter openings (Taconic Plastics, Inc., Petersburg, N.Y.) and submerged in a pan of 0.9 percent by weight sodium chloride solution at about 23° C., making sure that the screens are held down until the bags are completely wetted. After wetting, the samples remain in the solution for 30 minutes, at which time they are removed from the solution and temporarily laid on a nonabsorbent flat surface. The wet bags are then placed into the basket of a suitable centrifuge capable of subjecting the samples to a force equivalent to 300 times the acceleration of gravity. A suitable centrifuge is a Heraeus Instruments Labofuge 400, having a water collection basket, digital rotations per minute (rpm) gauge, and machined drainage basket adapted to hold and drain the samples. The samples must be placed in opposing positions within the centrifuge to balance the basket when spinning. The bags are centrifuged at a target of 1600 rotations per minute, but within the range of 1500-1900 rotations per minute, for 3 minutes (target force of 300 times the acceleration due to gravity). The bags are removed and weighed, with the empty bags (controls) being weighed first, followed by the bags containing the superabsorbent material or fiber. The amount of fluid absorbed and retained by the superabsorbent material or fiber, taking into account the fluid retained by the bag material alone, is the Centrifugal Retention Capacity of the superabsorbent material or fiber, expressed as grams of fluid per gram of material. This calculation is done by the following equation:

$$CRC=(W_s-W_e-W_d)/W_d$$

In this equation, "CRC" is the Centrifugal Retention Capacity of the sample (grans/gram), "$W_s$" is the after centrifuged mass of the teabag and the sample (grams), "$W_e$" is the average after centrifuged mass of the empty teabag (grams), and "$W_d$" is the dry mass of the sample (grams). The CRC measurements for each of three replicate are averaged to provide the CRC value of the material.

Vortex Time Test

The Vortex Time Test measures the amount of time in seconds required for a predetermined mass of a superabsorbent material to close a vortex created by stirring 50 milliliters of 0.9 by weight sodium chloride solution at 600 revolutions per minute on a magnetic stir plate. The time it takes for the vortex to close is an indication of the free swell absorbing rate of the superabsorbent material. As differences in centrifuge retention capacity (which can be dependent on particle size) between superabsorbent materials can affect the vortex time, the vortex time test can be compensated for better comparison of various superabsorbent materials by adjusting the amount of superabsorbent material added to the 50 milliliter sodium chloride solution as compared to a standard conventional superabsorbent.

This test was described in US 2003/0139715.

Briefly, the amount of superabsorbent material to be used in the vortex time test is determined by comparison of the centrifuge retention capacity of the new sample against a conventional superabsorbent material, such as FAVOR® 880, available from Stockhausen, Inc., Greensboro, N.C., which has a centrifuge retention capacity value of 33.6 g/g. For determining the vortex time of FAVOR® 880, 2.0 grams of FAVOR® 880 are added to 50 milliliters of 0.9 weight percent sodium chloride solution. The amount of a different superabsorbent material to be used in the vortex time test can be determined by the following equation.

$$C=(2.0 \text{ grams}\times A)/B$$

in this equation, "A" is the centrifuge retention capacity of the standard superabsorbent (FAVOR® 880), or 33.6 g/g, "B" is the centrifuge retention capacity of the second superabsorbent material, and "C" is the amount of the second superabsorbent material to be used in the vortex time test.

The vortex time test is preferably done at standard room atmosphere conditions, where the temperature is 23° C.±1° C. and relative humidity is 50 percent±2 percent. The vortex time test is done by measuring 50 milliliters (±0.01 milliliter) of 0.9 by weight sodium chloride solution into the 100 milliliter beaker. A 7.9 millitneters×32 millimeters TEFLON® covered magnetic stir bar without rings (such as that commercially available from Baxter Diagnostics, under the trade designation S/P® brand single pack round stirring bars with removable pivot ring) is placed into the beaker. A magnetic stir plate (such as that commercially available from PMC Industries, under the trade designation DATA-PLATE® Model #721) is programmed to 600 revolutions per minute. The beaker is placed on the center of the magnetic stir plate such that the magnetic stir bar is activated. The bottom of the vortex should be near the top of the stir bar. The superabsorbent material is pre-screened through U.S. standard #30 mesh and retained on U.S. standard #50 mesh. The superabsorbent material, therefore, has a particle size of between 300 and 600 microns. The required mass of the superabsorbent material to be tested is weighed out on weighing paper. While the sodium chloride solution is being stirred, the superabsorbent material to be tested is quickly poured into the saline solution and a stopwatch is started. The superabsorbent material to be tested should be added to the saline solution between the center of the vortex and the side of the beaker. The stopwatch is stopped and the time is recorded when the surface of the saline solution becomes flat. The time, recorded in seconds, is reported as the vortex time.

Results.

Comparative Example 1. Acrylic Acid Polymer without Fibril Reinforcement

The synthesis resulted in a clear gel with good resiliency. After drying and grinding, solid particles with sizes in the range of from about 300-600 μm were sieved and tested.

Example 1. Acrylic Acid Polymer with 5.5 wt % Halloysite Nanoclay Powder 5.5 wt % halloysite clay powder was added into the reaction mixture before polymerization. An opaque gel with white color and better resiliency compared to Comparative Example 1 resulted from the synthesis. This difference is due to the fine dispersion of clay particles within the gel matrix. After drying and grinding, solid particles with sizes in the range of from about 300-600 μm were sieved and tested.

Example 2. Acrylic Acid Polymer with 10 wt % Halloysite Nanoclay Powder 10 wt % halloysite clay powder was added into the reaction mixture before polymerization. A gel with more translucency compared to Example 1 resulted from the synthesis. Higher translucency is due to the higher loading level of halloysite clay powders. The gel demonstrated good resiliency. Dispersion of halloysite clay powder is good at a macro scale; a homogenous white color across the gel was observed. After drying and grinding, solid particles with sizes in the range of from about 300-600 μm were sieved and tested.

Example 3. Acrylic Acid Polymer with 15 wt % Halloysite Nanoclay Powder 15 wt % halloysite clay powder was added into the reaction mixture before polymerization. No obvious difference regarding the appearance of gel was observed during the synthesis process. After drying and grinding, solid particles with sizes in the range of from about 300-600 μm were sieved and tested.

Only the AUL was improved when the loading level of halloysite clay was increased from 10% to 15%; both the intake rate and CRC were reduced. The increase of AUL could be due to the reinforcing effect of halloysite day filler. The reduction of intake rate and CRC could be due to the barrier effect of clay in the acrylic add solution, which prevents the reaction between initiator and acrylic acid monomer during gelation process. In addition, the mixture of acrylic acid solution and halloysite clay at high loading levels could present high viscosity, leading to limited progression of polymerization. Therefore, the residual monomer within the SAM/halloysite composite could be higher for die SAM with high loading level of halloysite clay fillers, thereby leading to inferior absorption properties.

Example 4. Acrylic Acid Polymer with 5.5 wt % Nanofibrillated Cellulose

To investigate the influence of filler type on the absorbency properties of SAM composites, 5.5 wt % nanocellulose was added into the reaction mixture before polymerization. A uniformly white gel was synthesized. After drying and grinding, solid particles with sizes in the range of from about 300-600 μm were sieved and tested.

Unlike the halloysite clay, adding nanocellulose as a filler in the polyacrylic acid matrix led to slightly decreased or unchanged AUL. The CRC was similar to Comparative Example 1. These results indicate that there is no reinforcement from nanocellulose as filler. Without being bound by any particular theory, this could be due to the low elastic modulus of nanocellulose fiber.

TABLE 1

Properties of prepared SAMs. Comparative Example 1 and Examples 1 -4 were prepared from the same batch.

| Sample | Percent Filler (wt %) | Filler Morphology | Vortex Time (s) | AUL (g/g) | CRC (g/g) |
|---|---|---|---|---|---|
| Comparative Example 1 | 0 | N/A | 73 | 10.1 ± 0.5 | 29.8 ± 1.0 |
| Example 1 | 5.5 | Nanotubes | 67 | 14.9 ± 0.6 | 29.4 ± 0.4 |
| Example 2 | 10 | Nanotubes | 76.5 | 9.7 ± 0.5 | 32.2 ± 0.5 |
| Example 3 | 15 | Nanotubes | 98 | 10.5 ± 0.2 | 24.4 ± 0.2 |
| Example 4 | 5.5 | Nanofiber | 69 | 9.5 ± 0.9 | 29.2 ± 0.5 |

The data in Table 1 demonstrate that the absorption rate and AUL were improved after incorporating tube-like nanoclay to the SAM matrix. Without being bound by any particular theories, these improvements could be due to the change of gel structure, through interfacial adhesion from —OH bonding on clay edges and surfaces, and/or effective reinforcing influence of clay tubes or clay platelets, which increases gel strength during the absorption process.

Figure 1B:
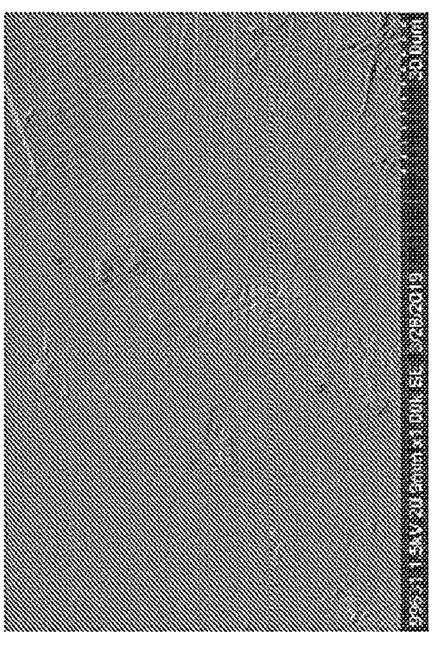
FIG. 1B is an exemplary embodiment of an SEM image of the morphology of a SAM/Halloysite composite in accordance with the present disclosure.
Figure 1C:
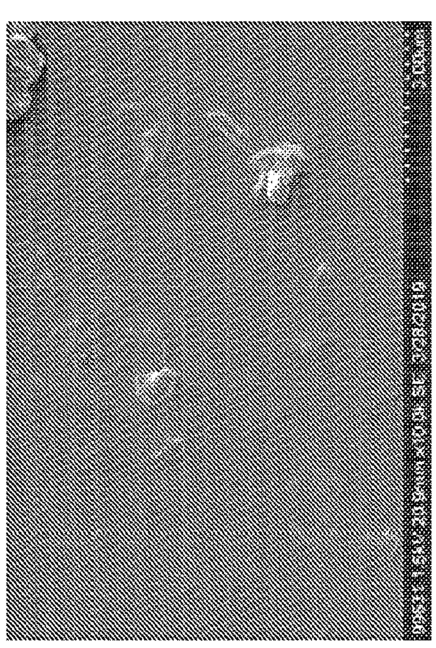
FIG. 1C is an exemplary embodiment of an SEM image of the morphology of a SAM control sample not in accordance with the present disclosure.
Figure 1D:
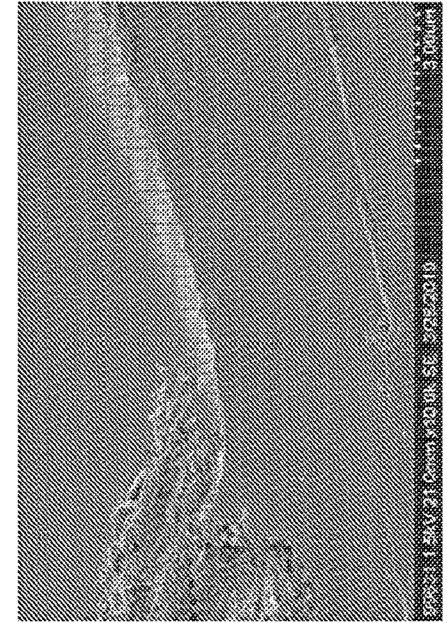
FIG. 1D is an exemplary embodiment of an SEM image of the morphology of a SAM/Halloysite composite in accordance with the present disclosure.

FIG. 1 shows the comparison of phase morphology between a conventional SAM control sample and a SAM/halloysite 94.5/5.5 clay composite sample. It can be seen that an agglomeration of halloysite day phase is dispersed within the SAM matrix, which indicates the existence of nanotube day as a reinforcing filler. Further improvement of absorption properties is expected when the dispersion of day is more homogenously exfoliated and dispersed.

Comparative Example 2. Acrylic Acid Polymer without Fibril Support

The synthesis resulted in a clear gel with good resiliency. After drying and grinding, solid particles with sizes in the range of from about 300-600 μm were sieved and tested.

Example 5. Acrylic Acid Polymer as with 5.5 wt % 1.34 TCN Nanoclay

To investigate the influence of filler type on the absorbency properties of SAM composites, 5.5 wt % 1.34 TCN nanoclay was added into the reaction mixture before polymerization. 1.34 TCN nanoclay has a plate-like morphology instead of a fibrillar structure. An opaque gel with slightly yellow color and better resiliency compared to Comparative Example 2 resulted from the synthesis. This could be due to the fine dispersion of clay particles within the gel matrix. After drying and grinding, solid particles with sizes in the range of from about 300-600 μm were sieved and tested.

TABLE 2

Properties of prepared SAMs. Comparative Example 2 and Example 5 were prepared from the same batch.

| Sample | Percent Filler (%) | Filler Morphology | Vortex Time (s) | AUL (g/g) | CRC (g) |
|---|---|---|---|---|---|
| Comparative Example 2 | 0 | N/A | 84 | 10.3 ± 0.3 | 35 ± 0.2 |
| Example 5 | 5.51 | Plate with thickness in nano range | 66 | 12.2 ± 0.9 | 29 ± 0.1 |

The AUL of Example 1 is higher than that of Example 5, which indicates that nanotube-like structures are more effective than plate-like structures. This is because plate-like structures are two-dimensional, while nanotube structures are one-dimensional, and the nanotubes have larger aspect ratios, which have a lower threshold to form a percolated structure.

As demonstrated herein, the absorbency rate was increased by 5-8%, AUL was improved by 21-48%, and CRC was decreased by 1-14% when the nanotube clay is used during synthesis in an amount less than 15%. Without being bound by any particular theory, the increase of AUL are believed to be due to the effective reinforcing influence of halloysite clay filler, which provides higher mechanical properties for SAM gel in a swollen state to retain the liquid under pressure.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. An absorbent composite comprising:

a superabsorbent material; and a fibril filler substantially distributed throughout the superabsorbent material, wherein the fibril filler has a diameter in the range of from about 1 nm to about 75 nm, wherein the fibril filler is in a form comprising nanotubes;

wherein the superabsorbent material consists of polyacrylic acid (PAA);

wherein the fibril filler has an elastic modulus greater than the elastic modulus of the superabsorbent material.

2. The absorbent composite of claim 1, wherein the fibril filler is present in an amount of less than about 15 wt %.

3. The absorbent composite of claim 1, wherein the fibril filler is uniformly distributed throughout the superabsorbent material.

4. The absorbent composite of claim 1, wherein the fibril filler comprises halloysite.

5. The absorbent composite of claim 1, wherein the absorbent composite further comprises a crosslinker.

6. A method of producing an absorbent composite, the method comprising:

forming a mixture comprising:

a polymerizable monomer of a superabsorbent material, wherein the polymerizable monomer is acrylic acids;

a fibril filler, wherein the fibril filler has a diameter in the range of from about 1 nm to about 75 nm, wherein the fibril filler is in a form comprising nanotubes;

water;

optionally a neutralization agent;

optionally an initiator, and optionally a crosslinker; and polymerizing the polymerizable monomer of a superabsorbent material in the mixture to produce an absorbent composite comprising a superabsorbent material and the fibril filler;

wherein the fibril filler is substantially distributed throughout the superabsorbent material in the absorbent composite; and wherein the superabsorbent material consists of polyacrylic acid (PAA)

wherein the fibril filler has an elastic modulus greater than the elastic modulus of the superabsorbent material.

7. The method of claim 6, wherein the fibril filler is present in the absorbent composite in an amount of less than about 15 wt %.

8. The method of claim 6, wherein the fibril filler is uniformly distributed throughout the superabsorbent material in the absorbent composite.

9. The method of claim 6, wherein the fibril filler comprises halloysite.

10. The method of claim 6, wherein the mixture is a homogenous mixture.

11. The method of claim 6, wherein the method step of forming a mixture comprises a method selected from the group consisting of stirring the mixture, cooling the mixture, heating the mixture, degassing the mixture, degassing the mixture with $N_2$, and combinations thereof.

12. The method of claim 6, wherein the method step of polymerizing the polymerizable monomer of a superabsorbent material in the mixture comprises adding an initiator to the mixture.

13. The method of claim 6, wherein the method further comprises adding an initiator to the mixture during polymerization.

14. A consumer product comprising an absorbent composite comprising a superabsorbent material and a fibril filler substantially distributed throughout the superabsorbent material, wherein the superabsorbent material consists of polyacrylic acid (PAA), wherein the fibril filler has an elastic modulus greater than the elastic modulus of the superabsorbent material, and wherein the fibril filler has a diameter in the range of from about 1 nm to about 75 nm, wherein the fibril filler is in a form comprising nanotubes.

15. The consumer product of claim 14, wherein the consumer product is selected from the group consisting of personal hygiene products, wipes, napkins, bibs, disposable bed liners, wound dressings, food packaging, baby and adult diaper products, child training pants, feminine pads, arm bands, agricultural and pet products that contain superabsorbent ingredients, disposable absorbent products, and combinations thereof.

* * * * *